US009976985B2

United States Patent
Wilks et al.

(10) Patent No.: US 9,976,985 B2
(45) Date of Patent: *May 22, 2018

(54) FIELD ASYMMETRIC ION MOBILITY SPECTROMETRY SYSTEM

(71) Applicant: Owlstone Medical Limited, Cambridge (GB)

(72) Inventors: Ashley Wilks, Stamford, CT (US); Matthew Hart, London (GB); Stephen Hartwell, Cambridge (GB); Alison Hart, Cambridge (GB); Lara E. Jamieson, Cambridgeshire (GB); Max Allsworth, Essex (GB); John Somerville, Hertfordshire (GB)

(73) Assignee: Owlstone Medical Limited, Cambridge (GB)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/160,761

(22) Filed: May 20, 2016

(65) Prior Publication Data

US 2016/0266067 A1 Sep. 15, 2016

Related U.S. Application Data

(63) Continuation of application No. 13/852,675, filed on Mar. 28, 2013, now Pat. No. 9,366,649.

(60) Provisional application No. 61/617,395, filed on Mar. 29, 2012.

(51) Int. Cl.
*G01N 27/62* (2006.01)

(52) U.S. Cl.
CPC ......... *G01N 27/624* (2013.01); *G01N 27/622* (2013.01)

(58) Field of Classification Search
USPC ........ 250/281, 282, 286–288, 290–292, 294, 250/297, 397
See application file for complete search history.

(56) References Cited

U.S. PATENT DOCUMENTS

| | | | |
|---|---|---|---|
| 6,495,823 B1 | 12/2002 | Miller | |
| 6,504,149 B2 | 1/2003 | Guevremont | |
| 6,509,562 B1 | 1/2003 | Yang | |
| 6,690,004 B2 | 2/2004 | Miller | |
| 6,770,875 B1 | 8/2004 | Guevremont | |
| 6,806,463 B2 | 10/2004 | Miller | |
| 7,005,632 B2 | 2/2006 | Miller | |
| 7,045,776 B2 | 5/2006 | Kaufman | |
| 7,057,168 B2 | 6/2006 | Miller | |
| 7,241,989 B2 | 7/2007 | Miller | |
| 7,355,170 B2 * | 4/2008 | Miller | G01N 27/622 250/281 |

(Continued)

*Primary Examiner* — Bernard Souw
(74) *Attorney, Agent, or Firm* — Sheppard, Mullin, Richter & Hampton LLP

(57) ABSTRACT

An apparatus, system and method for detecting, identifying, classifying and/or quantifying chemical species in a gas flow using a micro-fabricated ion filter coupled to a system adapted to apply drive signals to the ion filter. Coupled to the ion filter is a system adapted to measure the output of the ion filter, which in turn is coupled to a system adapted to extract numerical parameters from the measured output of the ion filter to facilitate chemical detection, identification, classification and/or quantification of the gas flow.

18 Claims, 8 Drawing Sheets

(56) References Cited

U.S. PATENT DOCUMENTS

| | | | |
|---|---|---|---|
| 7,576,319 B2* | 8/2009 | Miller | G01N 27/622 |
| | | | 250/281 |
| 7,714,278 B2 | 5/2010 | Boyle | |
| 7,855,360 B2 | 12/2010 | Fernandez de la Mora | |
| 8,278,622 B2 | 10/2012 | Fernandez de la Mora | |
| 8,319,177 B2 | 11/2012 | Boyle | |
| 9,366,649 B2* | 6/2016 | Wilks | G01N 27/624 |
| 2003/0052263 A1 | 3/2003 | Kaufman | |
| 2003/0132380 A1 | 7/2003 | Miller | |
| 2003/0146377 A1* | 8/2003 | Miller | G01N 27/624 |
| | | | 250/286 |
| 2005/0253061 A1 | 11/2005 | Cameron | |
| 2007/0176092 A1 | 8/2007 | Miller | |
| 2008/0128609 A1 | 6/2008 | Miller | |
| 2008/0191132 A1 | 8/2008 | Boyle | |
| 2008/0203290 A1 | 8/2008 | Fernandez de la Mora | |
| 2011/0006196 A1 | 1/2011 | Boyle | |
| 2011/0057096 A1 | 3/2011 | Fernandez de la Mora | |
| 2012/0319863 A1 | 12/2012 | Sato | |
| 2016/0266067 A1* | 9/2016 | Wilks | G01N 27/624 |

* cited by examiner

FIELD ASYMMETRIC ION MOBILITY SPECTROMETRY SYSTEM

CROSS REFERENCE TO RELATED APPLICATIONS

This application is a Continuation of U.S. patent application Ser. No. 13/852,675 filed on Mar. 28, 2013, which claims priority to U.S. Patent Application Ser. No. 61/617,395 filed on Mar. 29, 2012, all of which are incorporated herein by reference in their entirety.

FIELD OF THE INVENTION

The present invention relates to devices and methods for ion mobility systems. More specifically, the invention relates to a method and apparatus for detecting chemicals using a Field Asymmetric Ion Mobility Spectrometry (FAIMS) system.

BACKGROUND OF THE INVENTION

The ability to ionize gases using ion mobility systems is useful for a wide range of applications including many chemical detection applications. Ionization techniques, in which a gas sample is ionized and then separated into constituent parts that can be detected individually, are widely used for gas composition sensing. Two well-known examples are Ion Mobility Spectrometry (IMS) and Field Asymmetric Ion Mobility Spectrometry (FAIMS), also known as Differential Mobility Spectrometry (DMS). Ion mobility detection techniques tend to be very well suited to measuring trace constituents of gas mixtures that often consist of a carrier gas with additional gases mixed in at low concentrations (for example part-per-million or part-per-billion levels). Ion mobility techniques can also be used effectively over a range of gas pressures, including pressures close to one atmosphere. This makes them useful for, amongst other things, measuring low-level impurities in air. Because they work by measuring properties of ionized molecules and because gas samples for analysis generally consist mainly of neutral molecules, ion-mobility-based detectors generally incorporate an ionizer. The sample gas is passed through the ionizer to produce a population of ionized molecules that are then manipulated in some way involving separation or selection of ionized molecules according to their behavior in an electric field, before being detected. Ionizers commonly in use include radioactive sources, light-based devices such as ultra-violet lamps, and electrostatic devices such as corona discharge ionizers.

Practical chemical detectors such as Field Asymmetric Ion Mobility Spectrometry (FAIMS) systems compensate for varying environmental conditions as these can affect the output of the spectrometer. There are also a number of implementation challenges that the designer must overcome in order to produce a repeatable and reliable detection system. As one skilled in the art would recognize, a wide variety of non-idealities are encountered in practice. For instance, some of those most relevant to FAIMS systems fall into the following categories:

Environmental and system variations and non-uniformities (e.g. changes in temperature, pressure, humidity and pump rate);

Non-ideal device physics (e.g. charge mirroring); and

Operational constraints (e.g. must provide certain levels of efficiency and stability while maintaining performance).

In this regard, it is to be understood and appreciated changes in ambient conditions such as temperature, pressure, and ambient humidity often lead to changes in FAIMS spectra. It is noted theoretical and/or empirical corrections exist for these effects. While theoretical approaches work well for pressure and, to a lesser extent, temperature, not all environmental conditions can easily be corrected in this manner. Empirical corrections can be determined for all ambient variables, but this approach necessitates prior characterization of analytes across a multi-dimensional matrix of conditions and the storage of this data for each analyte, which can be a time consuming and laborious process. It is thus desirable to provide a system or approach that enables conditions at the sensor head to be controlled in such a system such that each analyte only has to be characterized under a small set of environmental conditions.

In regards to a FAIMS system, since it is a highly sensitive system, FAIMS spectrometers often detect down to parts-per-billion levels or more. Direct sampling from the ambient environment can thus be problematic for such highly sensitive systems, as they can be saturated by higher concentrations of analytes or interferents, thus hiding the analytes of actual interest. High concentrations of some analytes can persist within the system as contamination due to absorption onto internal surfaces, adversely affecting performance.

It is to be further understood that in Ion Mobility Spectrometry (IMS) systems (which work at a constant electric field) the peak location is used as an identifier and the parameter of Reduced Mobility ($K_0$) "factors" response variations due to temperature and pressure. Previous DMS/FAIMS systems (which work under variable electric field) have used the $E_C:E_D$ spectrum for identification but operate over a much limited field range (35 kV·cm$^{-1}$ c.f. 75 kV·cm$^{-1}$).

SUMMARY OF THE INVENTION

The purpose and advantages of the invention will be set forth in and apparent from the description that follows. Additional advantages of the invention will be realized and attained by the devices, systems and methods particularly pointed out in the written description and claims hereof, as well as from the appended drawings.

One aspect of the invention relates to an apparatus, system and method for detecting, identifying, classifying and/or quantifying chemical species in a gas flow using a microfabricated ion filter coupled to a system adapted to apply drive signals to the ion filter. Coupled to the ion filter is a system adapted to measure the output of the ion filter, which in turn is coupled to a system adapted to extract numerical parameters from the measured output of the ion filter to facilitate chemical detection, identification, classification and/or quantification of the gas flow.

Other aspects of the invention is that inclusion of a FAIMS system in which the output of the FAIMS system is a two dimensional plot indicating the signal as a function of the RF voltage (Dispersion Field—$E_D$) and the compensation voltage (Compensation Field—$E_C$). This plot is used to discriminate between different chemicals. With reference to FIG. 1A, shown is an example $E_C:E_D$ matrix (Dispersion Spectrum) in which the spectrum is reduced to its Gaussian components (Peak Ion Current; Peak Width and Peak Position) and each discrete $E_D$ point.

It is to be appreciated that another aspect of the present invention relates to finding information from plots characteristic of individual chemicals. An apparatus and method is provided to process variations induced by ambient conditions (specifically pressure, temperature and humidity). It is to be understood that when more than one species is present, chemical interactions and competitive ionization causes changes to both the spectra and signal strength. A noted advantage over the prior art is that the electric field strength translating to the Dispersion Field ($E_D$) can be much higher, causing fragmentation of molecules. Fragmentation patterns provide characteristic, molecular specific classification features.

BRIEF DESCRIPTION OF THE DRAWINGS

The accompanying appendices and/or drawings illustrate various non-limiting, example, inventive aspects in accordance with the present disclosure.

WRITTEN DESCRIPTION OF CERTAIN EMBODIMENTS OF THE INVENTION

Figure 1A:
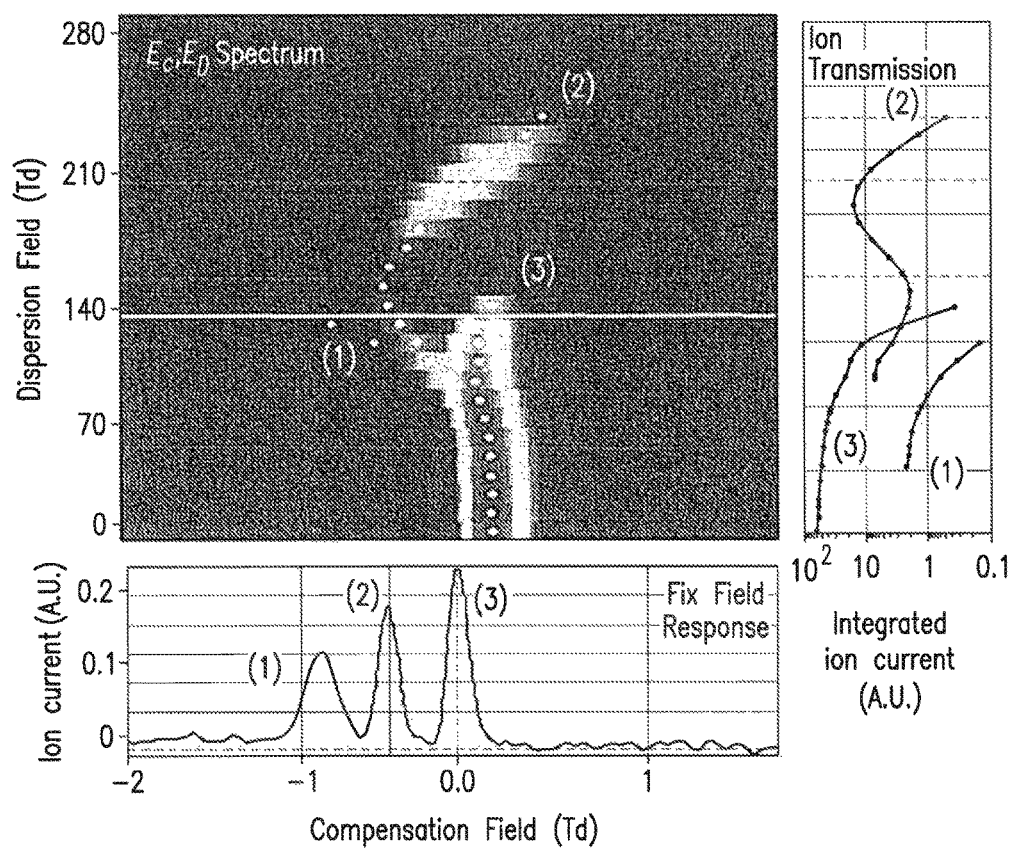
FIG. 1A illustrates a Compensation Field-Dispersion Field matrix.

The present invention is now described more fully with reference to the accompanying drawings, in which an illustrated embodiment of the present invention is shown wherein like reference numerals depict like elements. Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

Figure 1B:
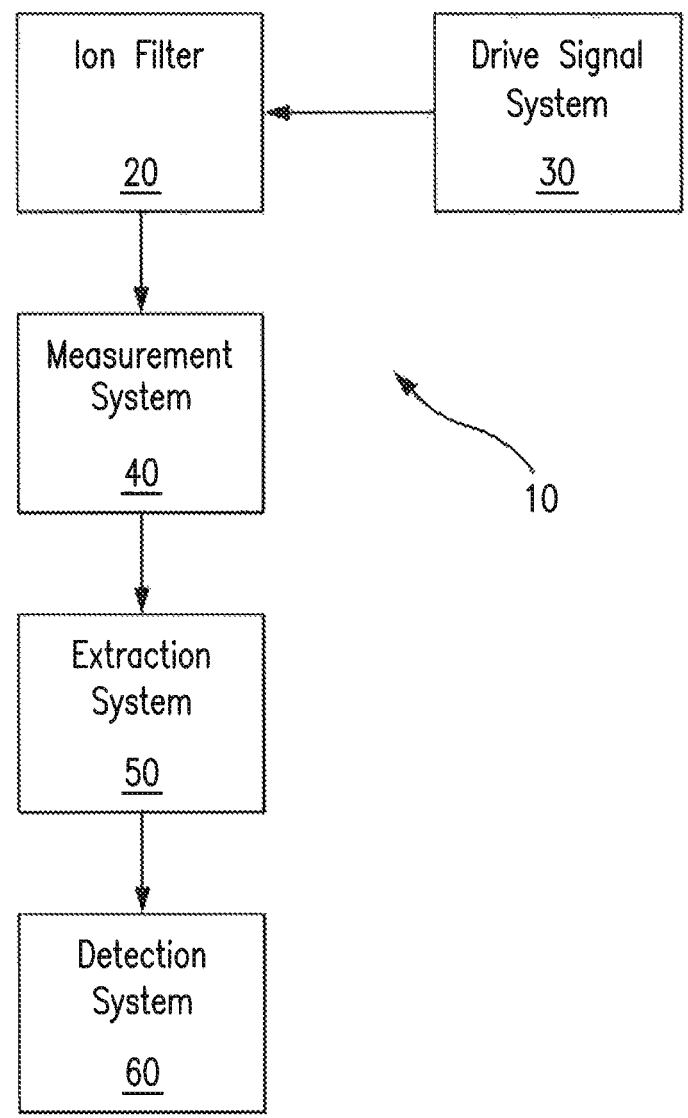
FIG. 1B illustrates a system overview of an illustrative embodiment of the invention.

With reference now to FIG. 1B, an illustrative embodiment of the invention is shown as a device for detecting, identifying, classifying and/or quantifying chemical species in a gas flow, depicted generally by reference numeral 10. Device 10 includes a micro-fabricated ion filter 20 for separating ions in a gas flow. Preferably, filter 20 uses (but is not to be understood to be limited thereto) Field Asymmetric Waveform Ion Mobility Spectrometry (FAIMS) for separating ions. Examples of which can be found in commonly-assigned U.S. Pat. No. 7,498,570 entitled: ION MOBILITY SPECTROMETER; U.S. Pat. No. 7,714,277 entitled: SMART FAIMS SENSOR; U.S. Pat. No. 8,258,466 entitled: SMART FAIMS SENSOR; U.S. Pat. No. 8,227,749 entitled: PULSED FLOW ION MOBILITY SPECTROMETER; U.S. Patent Publication No. 2010/0148051 entitled: ION FILTER; PCT Publication Nos. PCT/2012/002843 entitled: SENSOR APPARATUS AND METHOD FOR USE WITH GAS IONIZATION SYSTEMS; PCT/2013/000404 entitled: FIELD ASYMMETRIC ION MOBILITY SPECTROMETRY FILTER; PCT/2012/065171 entitled: SENSOR APPARATUS AND METHOD FOR USE WITH GAS IONIZATION SYSTEMS; PCT/2013/020131 entitled: FIELD ASYMMETRIC ION MOBILITY SPECTROMETRY FILTER and PCT/2012/002856 entitled: CORONA IONIZATION DEVICE AND METHOD, each of which are hereby incorporated by reference in their entirety.

Device 10 further includes a drive signal system 30 for applying drive signals to the ion filter 20 and a measurement system 40 for measuring the output of the ion filter 20. An extraction system 50 is coupled to measurement system 40 adapted and configured to extract numerical parameters from the measured output 40 of the ion filter 20. A detection system 60 is preferably coupled to the extraction system 50 being adapted and configured to facilitate chemical detection, identification, classification and/or quantification of the gas flow of ion filter 20.

As described further below, it is to be understood and appreciated that device 10 is adapted to use measurements of ion current as a function of one or more of compensation field and dispersion field to facilitate chemical detection, identification, classification and/or quantification which may preferably include the use of one or more ion peaks in FAIMS spectrum. It may further be adapted to classify ion peak trajectories into one or more of a number of categories and to use characteristic features of the trajectory of one or more ion peaks in the FAIMS spectrum to facilitate chemical detection, identification, classification and/or quantification wherein the characteristic features include ion peak position at one or more dispersion field values. Additionally, the characteristic features may be attributable to one or more of: ion fragmentation, dimer breakdown, monomer resurgence, monomer breakdown, field heating or changes in ion mobility. The characteristic features may include a point at which the gradient of compensation field versus dispersion field changes sign and/or a change in one or more peak characteristics at or in the vicinity of a particular dispersion field wherein the one or more peak characteristics include peak width and/or peak height. The one or more peak characteristics may further include peak location.

In additional embodiments of the invention, the rate of gas flow through the ion filter 20 is adjustable wherein the rate of gas flow is preferably selected to achieve a desired sensitivity and/or selectivity. Additionally, device 10 uses the relative peak amplitudes at a plurality of sample flow dilutions to infer one or more relative affinities wherein the one or more inferred relative affinities is preferably used to calculate one or more quantification correction factors. Still further, the one or more inferred relative affinities is used in combination with one or more identified or partially identified chemical responses to calculate the affinity of unknown analytes to facilitate detection, identification, classification and/or quantification.

Additional embodiments of the invention are to be understood to include using measurements of ion current as a function of one or more of compensation field and dispersion field. Device 10 may monitor a vicinity of a reactant ion peak to detect and/or device 10 uses the presence of a dimer peak to facilitate chemical detection, identification, classification and/or quantification. Further, device 10 may use the dispersion field value at which a monomer peak undergoes one or more of; a characteristic shift in compensation field position, a split into two or more separate peaks to identify a point of monomer fragmentation. Device 10 may also be adapted and configured to use measurements of peak width along the dispersion field axis wherein the device 10 uses the dispersion field and compensation field co-ordinates of a point at which ion current drops below a threshold value to facilitate chemical detection, identification, classification and/or quantification.

Other embodiments of the invention may include using a character table and/or characteristic table to associate features of the spectrum with one or more classes of analytes to facilitate chemical detection, identification, classification and/or quantification wherein the features include one or more of dimer breakdown, monomer resurgence, a turning point in peak trajectory, monomer zero compensation field crossing point, and other FAIMS spectral features. Device 10 may be adapted and configured to compare analyte peak position to a position of the reactant ion peak to compensate for environmental effects wherein an analyte peak property is used in combination with a reactant ion peak property to ascertain identity, class and/or concentration of the analyte. Device 10 may further use an analyte peak property in conjunction with a reactant ion peak property to ascertain identity, class and/or concentration of the analyte.

It is also to be understood and appreciated the device 10 is operational such that the width of the ions species peak under zero dispersion field conditions is estimated by extrapolating from the measurements of the width under two or more non-zero field conditions wherein signal levels are normalized to the reactant ion peak intensity or total ion current and wherein one or more applied fields are adjusted to account for changes in number of molecules per unit volume of gas in proximity to the FAIMS ion filter 20. Further, a number of molecules per unit volume are calculated by applying Van der Waal's equations for one or more gaseous components.

Device 10 may be further operational such that the relationship between peak parameters at a plurality of dispersion field frequencies is used to facilitate chemical detection, identification, classification and/or quantification wherein the region of the spectrum at which peak width starts to increase is also used to facilitate chemical identification, classification and/or quantification.

Device 10 may be adapted to adjust the frequency of the dispersion field waveform to modify the effects of humidity on resulting spectrum. The relationship between two peak intensities may be used to facilitate chemical detection, identification, classification and/or quantification. Device 10 may use the dispersion field value at which a dimer peak falls below a threshold value to identify a point of dimer breakdown and/or use an increase in a monomer peak intensity above a certain threshold dispersion field to confirm dimer breakdown to facilitate chemical detection, identification, classification and/or quantification wherein the relationship between the two peak intensities is that of one peak increasing while the other decreases and wherein the dispersion field is adjusted to account for changes in one or more of pressure and the effective temperature of ions.

Device 10 may further detect and use changes in peak properties as a function of one or more of compensation field and dispersion field to infer a value for the mobility of an ion species, and/or device 10 may further detect and use the inferred mobility value associated with ion trajectory to create a temperature dependent correction factor that can be applied to the trajectory to facilitate chemical detection, identification, classification and/or quantification.

With the basic components of device 10 in accordance with an illustrated embodiment being described above, particular features of the present invention is further provided below.

In accordance with an embodiment of the invention, it is to be understood that by extracting the peaks (i.e. their Gaussian parameters) on each Compensation Field ($E_C$) line the path of a particular chemical is tracked. It is noted there are various different types of information that can be extracted from a chemical track, which are discussed below and can be used in singly or in combination depending on the degree of similarity of the chemicals under test.

Figure 2:
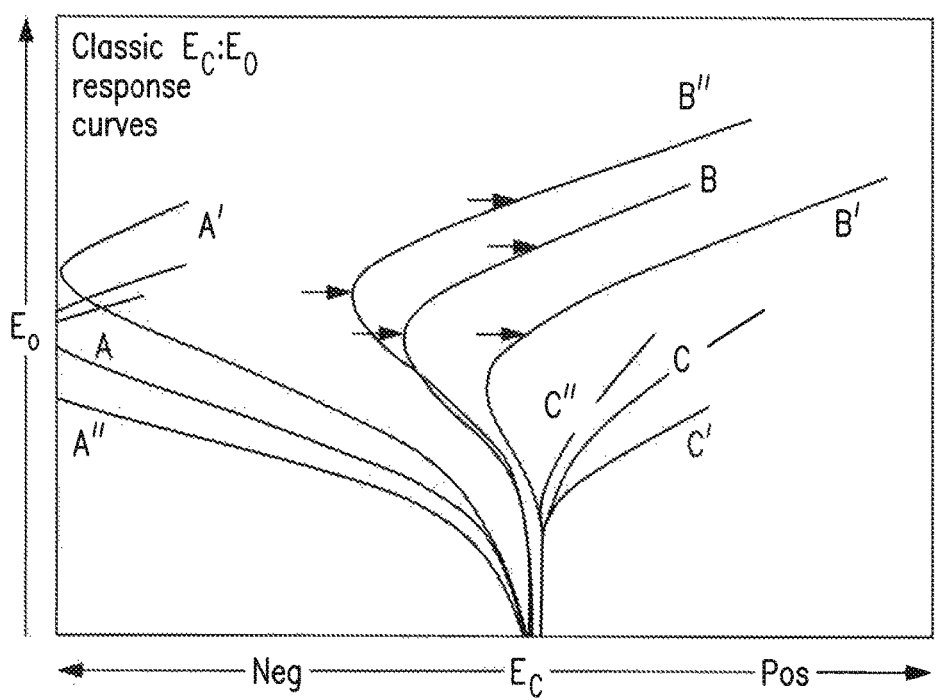
FIG. 2 illustrates peak trajectories for Type A, B & C ions.

With regards to the peak trajectories shown in FIG. 2, it is to be understood both positive ions and negative ions derived from unknown chemicals samples and introduced to an analytical system can be placed into three broad categories (Type A, B, C) depending on the shape of their trajectory. It is noted this a broad and basic form of categorization. Specific, features of use, include (but are not limited to) those listed below.

Track Inflection/Crossing Points/End Points

It is to be appreciated the Point of Inflection, Zero Crossing Point and End Point can be used to distinguish chemicals. The Point of Inflection is the point at which a curve turns back on itself. In the above example of FIG. 2, the leftmost point of each blue line is the point of inflection for that curve. It is noted the point of inflection is a distinctive feature (most chemical trajectories have a point of inflection) notable exceptions are the RIP and some dimer peaks. The Zero Crossing Point is the point at which the peak trajectory crosses 0 CV. Hence, it is specific to Type B compounds. Note that under different conditions, such as differing humidity levels, a chemical can exhibit Type B or Type C behaviour. The End Point is the point at which the peak trajectory drops below a detection threshold for the peak.

Additionally, chemicals can be identified by matching the unknown track against previously collected tracks of known chemicals, which is termed Peak Location. It is to be understood the peak height (or area) plotted along the track of the peak contains distinctive features. Analytical systems in accordance with the present invention preferably operate at much higher fields ($E_D$) and the $E_D$ dependant ion transmission contains much richer information than prior art systems (the kinetic and thermodynamic properties of ions are revealed and since these are molecular specific useful classification features are derived).

In accordance with the algorithm, the $E_D/N$ scale may be converted to effective ion temperature and $T_{eff}$ scales to $(E_D/N)^2$.

$$T_{eff}=T+\zeta \cdot M \cdot K_{(E/N)}^2 \cdot N_0^2 (E_D/N)^2/(3k_b)$$

Figure 3:
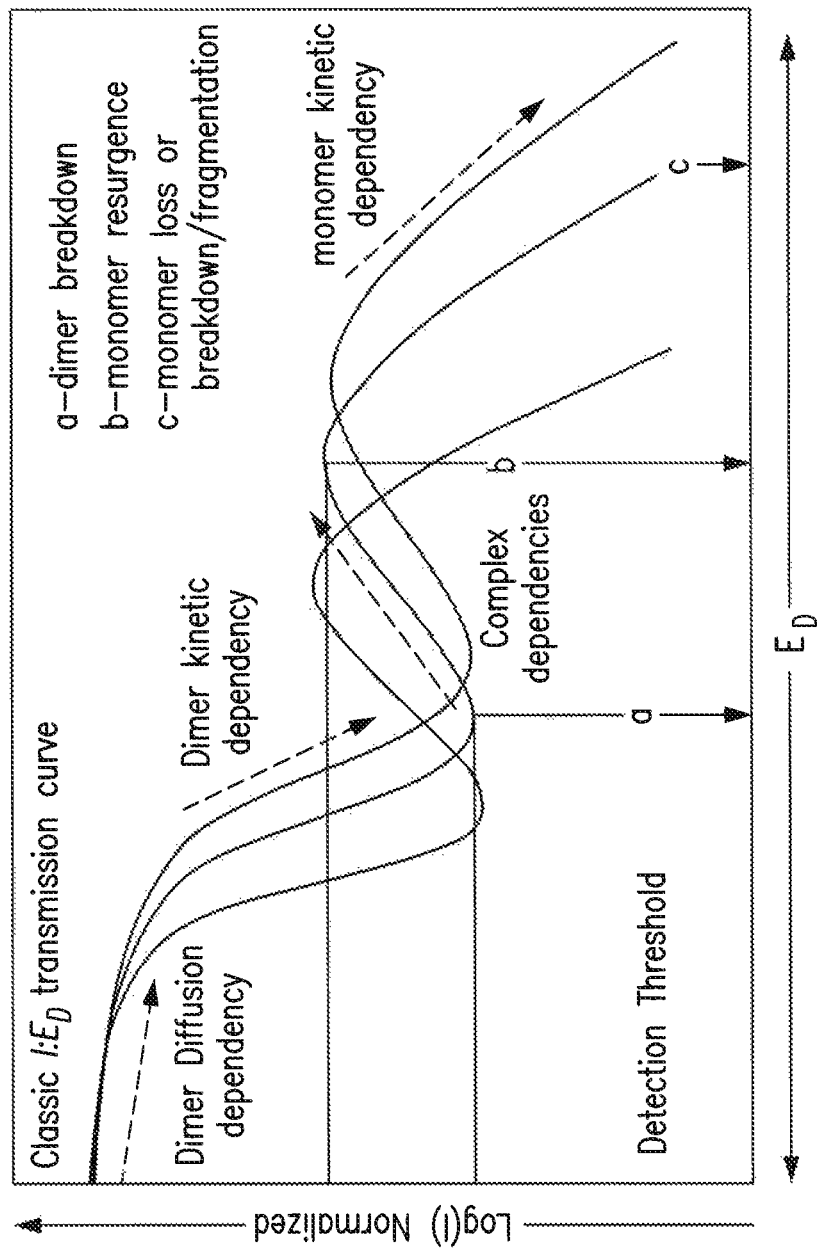
FIG. 3 illustrates integrated ion transmission Spectra.
Figure 4:
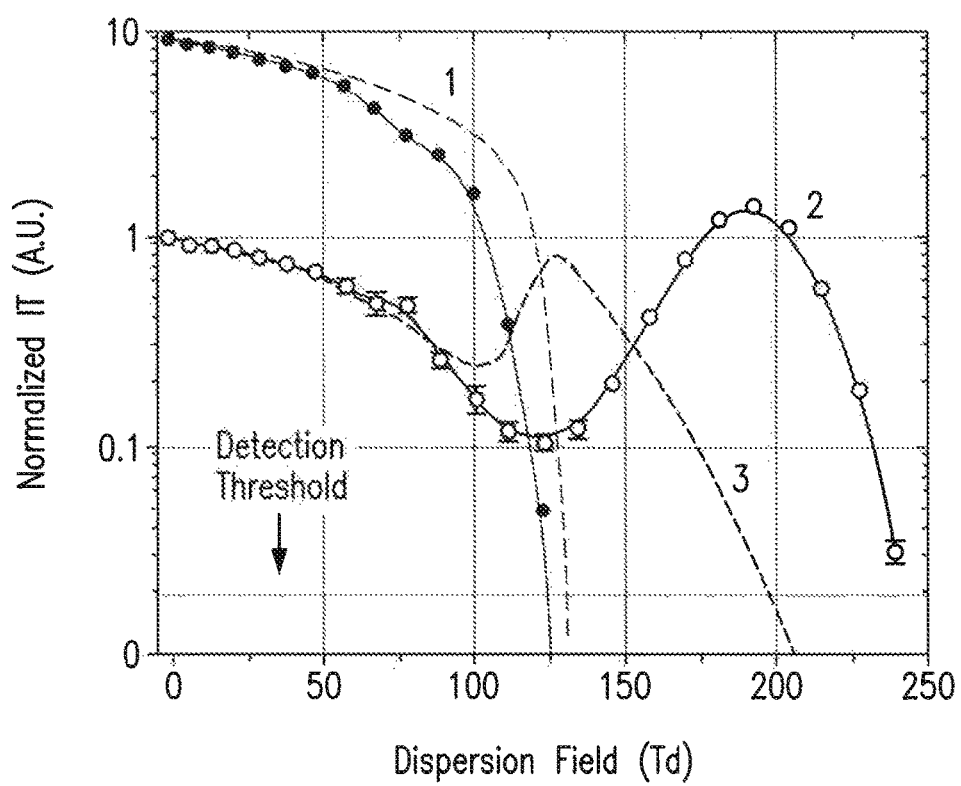
FIG. 4 illustrates ion transmission spectra.

With reference to FIGS. 3 and 4, shown is an Integrated Ion Transmission Spectra (FIG. 3) and Resolved Ion Transmission spectra (FIG. 4). This information is utilized to confirm the identity of a chemical or inferring information about its nature. Specifically the classification features of interest are:

I. Dimer Formation—not all chemicals form dimers so this provides a degree of discrimination.
II. Dimer Breakdown—the location and shape of the ion current curve at the dimer breakdown is indicative of the chemical(s) involved.
III. Monomer Resurgence—at high fields dimers are unable to form and the signal from the monomer will increase.
IV. Monomer Fragmentation—the monomer fragmentation occurs at high-field and as such provides information not available to prior art systems.

Figure 5:
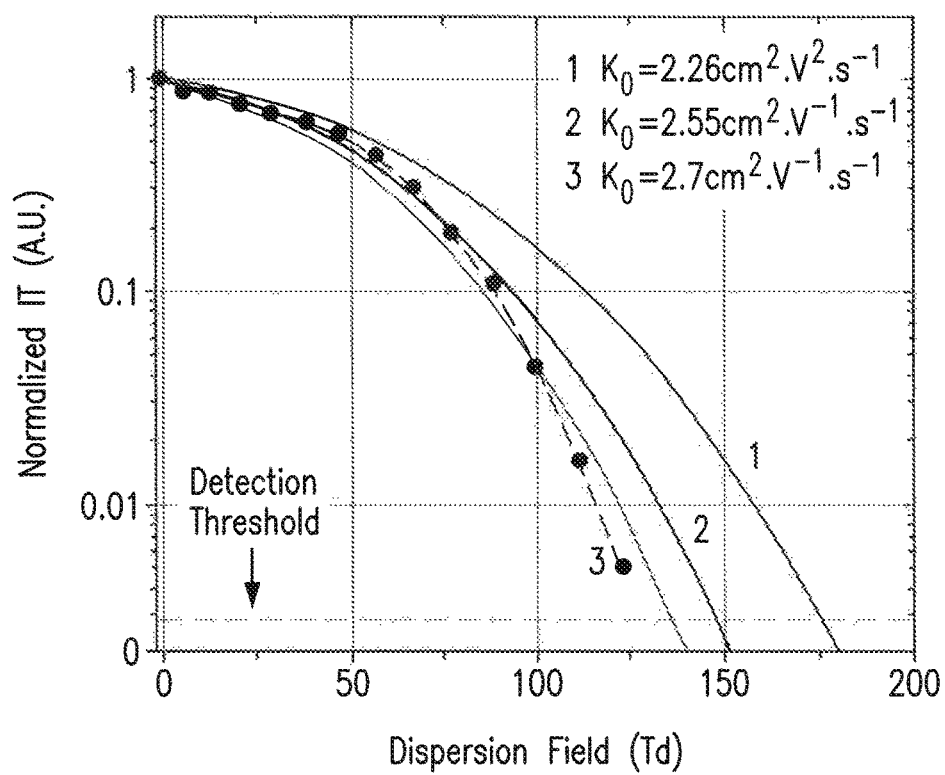
FIG. 5 illustrates transmission spectrum for non-fragmenting ions.

Additionally, physical constants for the ion generated from the chemical may be determined and include:

V. Ion mobility ($K_0$)—(with reference to FIG. 5) Ion mobility ($K_0$) may be derived by a fit of empirical data to the following equation. $K_0$ is extracted from the $g_{eff}$ term in the following fit to the data:

$$A_I = A_{I(in)} \cdot Q \cdot \exp(-t_{res} \cdot \pi^2 \cdot D_{II}/g_{eff}^2)$$

Figure 6:
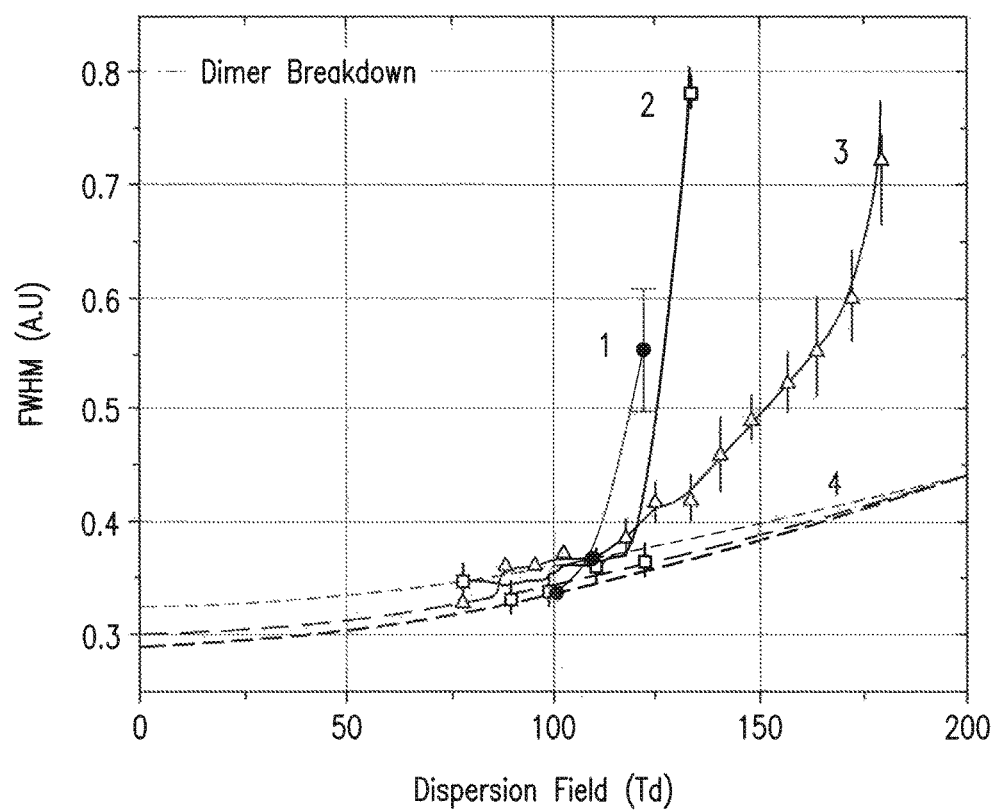
FIG. 6 illustrates peak width vs $E_D$ for dimer ions.

VI. Collisional efficiency factor ($\zeta$)—$\zeta$ may be determined from an analysis of the transmission profile and trajectory over a range of gas temperatures
VIII. Peak width—it is noted the peak width plotted along the track can also contain distinctive information
IX. Ion mobility ($K_0$)—Ion mobility at zero field is preferably defined by:

$$K_0 = \frac{16 N \ln 2 \cdot k_b T}{N_0 \cdot \text{qt}_{res} \cdot W_{1/2}^2}$$

Wherein the zero field peak width ($W_{1/2}$) may be determined from an extrapolation of peak widths over a portion of the $E_C:E_D$ spectrum back to zero $E_D$.
X. Ion breakdown field—it is noted the peak width turns exponential near the breakdown field. See FIG. 6 which illustrates Peak width vs $E_D$ for dimer ions of Acetone, Butanone and DMMP wherein near dimer breakdown peak width turns exponential.

Additional features of the present invention include:

Environmental Correction/Compensation

It is to be appreciated that environmental conditions affect the track and the ion current (which is important for quantification). A noted tool for this purpose is the track called the RIP (Reactant Ion Products) which are the ions of nitrogen, oxygen and water that are ionised along with the sample of interest.

Normalize Ion Current Against RIP

As the quantity of ions is set by the ionisation method and the other ions that are presently working with ion currents normalised against the RIP will enable more accurate quantification. In practice the chemical ion current is scaled against the height of the peak at low DF.

Normalize Location Against RIP

By measuring peak locations relative to the RIP it is possible to reduce the effect of environmental changes. This is likely to be most useful for humidity as temperature and pressure can be compensated for via physical models.

Compare RIP to Chemical Behavior

If there are chemicals with high electron/proton affinities present, the RIP will change characteristics enabling identification.

Effective Temperature and/or Pressure

It is noted that one method of finding chemical tracks that are invariant to ambient conditions is to use a y-axis scale that corresponds to the effective temperature and/or pressure. This includes a contribution from heating by the high field RF. Townsend units (i.e. field over number density—E/N), the effective ion temperature ($T_{eff}$) and the ion neutral collisional efficiency factors ($\zeta$) may be used in the correction of temperature and/or pressure.

Humidity Banding

If compensation for humidity cannot be achieved then it is preferable to operate the device at a small number of fixed humidities which rules specific to each fixed humidity.

Flow Rate Changes

It is to be appreciated that flow rate changes allow improved sensitivity (important when working near the detection limit) and can also be used to confirm if a high affinity chemical is present.

Improved Townsend Correction

Townsend correction divides the electric field by the number density of the gas. Normally the calculation of the number density is performed by assuming that all the gases are ideal. In accordance with an embodiment of the invention, improved results are obtained by using van der Waal's equations for each component.

Higher Frequency Operation

It is noted that the impact of humidity on chemicals is thought to be due to the formation of clusters of water molecules around the chemical of interest in the low field and the breaking up of them in the high field. In accordance with an embodiment of the invention, by using higher frequencies the chemicals preferably remain clustered thus reducing the variability.

Using Characteristic Tables

It is to be appreciated that in the same way that Infra-Red is able to map specific frequencies to particular bonds, in accordance with an embodiment of the invention, particular tracks are associated with classes of molecules. This has been mentioned above regarding identifying chemicals as Type A, B or C. For instance, a non-exhaustive example of a UH-FAIMS character Table is shown below as:

| Class | Analyte | Ion Mode | Chem. Functionality | Test Conc. Range | Gross Classification Rule |
|---|---|---|---|---|---|
| Nerve Agent | Tabun (GA) | Pos & Neg | Complex organo-phosphate | 0.1-1.0 mg · m$^{-3}$ | B, C |
| Nerve Agent | Sarin (GB) | Pos | Complex organo-phosphate | 0.1-1.0 mg · m$^{-3}$ | B, C |

-continued

| Class | Analyte | Ion Mode | Chem. Functionality | Test Conc. Range | Gross Classification Rule |
|---|---|---|---|---|---|
| Nerve Agent | Soman (GD) | Pos | Complex organo-phosphate | 0.1-1.0 mg·m$^{-3}$ | B, C |
| Nerve Agent | VX | Pos & Neg | Complex organo-phosphate | <0.1 | B, C |
| Blister Agent | Sulfur Mustard (HD) | Neg | Reactive organo chloro-sulfide | 0.1-2.0 mg·m$^{-3}$ | B, C |
| Blood/TIC | Hydrogen Cyanide (HCN) | Neg | Reactive LMW inorganic | 12-90 mg·m$^{-3}$ | A |
| Blood/TIC | Cyanogen Chloride (CNCl) | Neg | Reactive LMW inorganic | 2.5-50 mg·m$^{-3}$ | A (& B) |
| Nerve Simulant | Dimethyl methyl phosphonate (DMMP) | Pos | Stable organophos. | 0.7-5.7 mg·m$^{-3}$ | B, C |
| Blister Simulant | 2-chloroethyl ethyl sulphide (2-CEES) | Pos | Stable organo-chloro-sulfide | 0.1-2.0 mg·m$^{-3}$ | B, C |
| Blister Simulant | Methyl Salicylate (MS) | Pos & Neg | Stable aromatic ester | 0.1-2.0 mg·m$^{-3}$ | B |
| Interferant (cleaning agent solvent) | Dipropylene Glycol Monomethyl Ether (DPGME) | Pos | Stable complex glycol | 0.1-1.0 mg·m$^{-3}$ | B, C |
| Interferant of ARDROX * | 2, 4 methyl-pentandiol | Pos | Diol | 0.1-1.0 mg·m$^{-3}$ | B, C |
| Interferant of floor striper * | Monoethanol-amine | Pos | Hydroxyl-amine | Low <1 mg·m$^{-3}$ | B, C |
| Diesel Exhaust * | VOC/SO$_x$ & NO$_x$ mix | Pos & Neg | Hydrocarbon mix | — | A, C |
| Interferant of AFFF | Diethylene glycol mono butyl ether | Pos | Stable complex glycol | Low <1 mg·m$^{-3}$ | B, C |
| TIC | NH$_3$ | Pos | Reactive LMW inorganic | <1-100 ppm | A |
| TIC | Acrylonitrile (AcCN) | Neg | Reactive organo-cyanide | 11-190 ppm | A, B |
| TIC | Hydrogen Sulfide (H$_2$S) | Neg | Stable LMW inorganic | 10-138 ppm | B |
| TIC | Chlorine (Cl$_2$) | Neg | Reactive LMW inorganic | 7-50 ppm | A (& B) |
| TIC | Hydrogen Chloride (HCl) | Neg | Reactive LMW inorganic | 7-50 ppm | A (& B) |
| TIC | Mono-methylamine | Pos | Amine | <0.1-5.0 ppm | B |
| VOC | Acetone | Pos | Ketone | 0.2-2.1 mg·m$^{-3}$ | B, C |
| VOC | Butanone | Pos | Ketone | 0.3-3.2 ppm | B, C |
| VOC | 1-Butanol | Pos | Alcohol | 0.2-3.2 ppm | B, C |
| VOC | Iso-pentanol | Pos | Branched alcohol | Low ppm | B, C |
| VOC | Acetoin | Pos | Hydroxy ketone | Low ppm | B, C |
| VOC | Diacetyl | Pos | Diketone | Low ppm | B, C |
| VOC | Isoprene | Pos | Unsaturated hydrocarbon | Low ppm | B, C |
| VOC (nitro) | Nitromethane (CH$_3$NO$_2$) | Pos | Stable Nitro | 2.5-15 mg·m$^{-3}$ | B |
| VOC (nitro) | Dinitrotoluene (DNT) | Pos & Neg | Stable aromatic Nitro | 0.5-39 mg·m$^{-3}$ | B, C |

UH-FAIMS Character Tables

Figure 7:
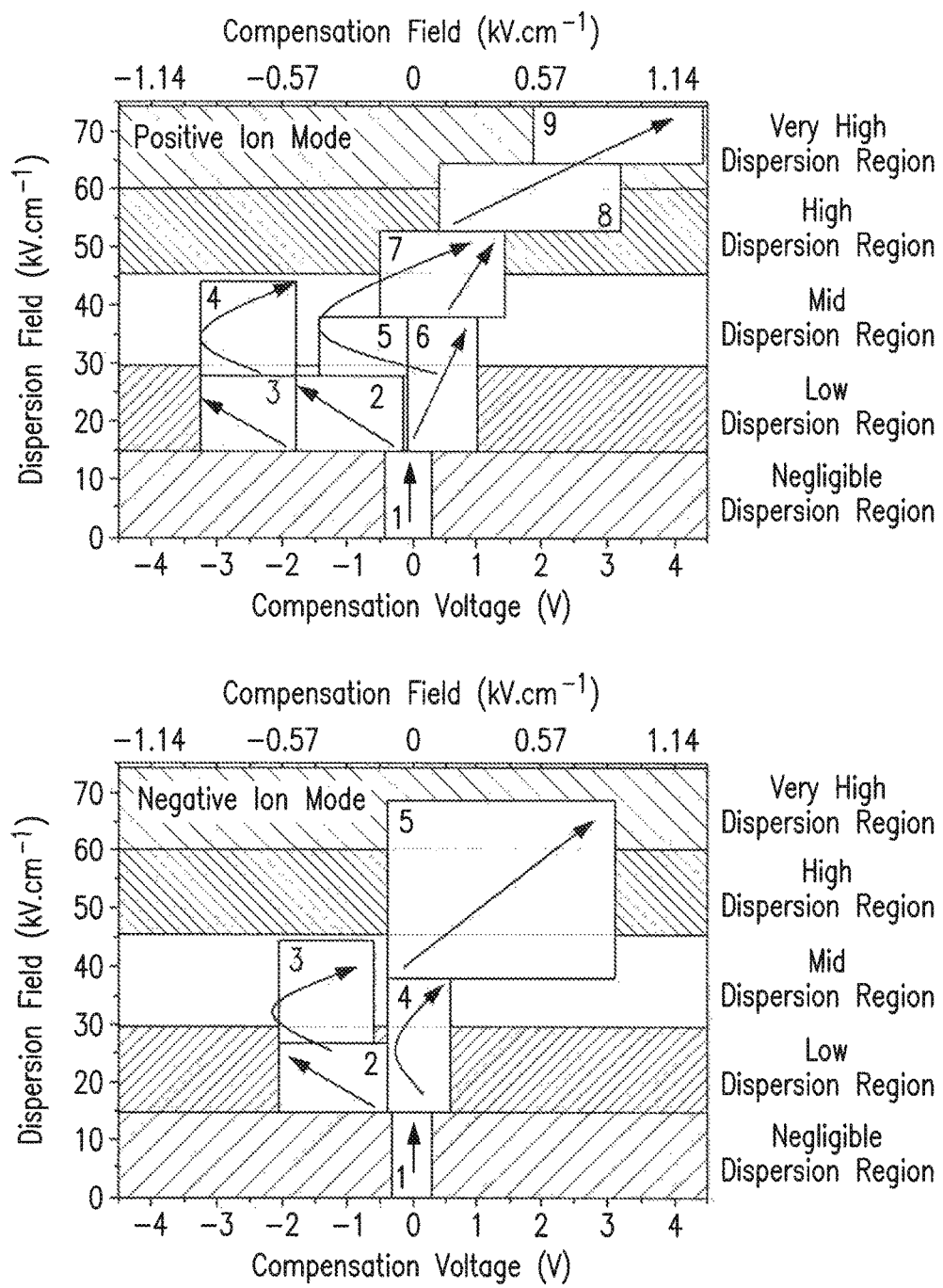
FIG. 7 illustrates positive and negative ion mode spectral character tables.

It is to be appreciated Character Tables are used in many forms of molecular spectroscopy to qualitatively define where different types of functional molecules give discrete responses in different parts of the available spectral window. They start off basic and become more detailed as more data is available, as illustrated in the positive and negative ion mode spectral character tables depicted in FIG. 7 and in the below UH-FAIMS character tables wherein table 1 depicts Discrete $E_C$:$E_D$ and response windows in the PIM and table 2 depicts discrete $E_C$:$E_D$ and response windows in the NIM.

TABLE 1

| Window | Key Information in this window-Peak Behavior (vs $E_D$) | e.g,. Agents responding in this Window |
|---|---|---|
| 1 | Strong accentuation of Zero field Ion Current compared to absence of agent ITS is fairly flat in this region | All PIM responders |
| 2 | Ion transmission Turn in peak trajectory of low MW agents-resolution from RIP | Low MW agents and agents that form stable fragment ions (Acrylonitrile, nitromethane) |

TABLE 1-continued

| Window | Key Information in this window-Peak Behavior (vs $E_D$) | e.g,. Agents responding in this Window |
|---|---|---|
| 3 | Sharp negative trajectory of Low MW agents<br>Monomer turning point of intermediate MW agents | All PIM responders |
| 4 | All Dimer responses<br>Dimers of smaller molecules begin to breakdown | PIM responders bar those that do not form stable dimers (Low MW agents) |
| 5 | Monomers of lower MW PIM responders | Low MW agents, Ion clusters of molecules that form stable fragment ions (Acrylonitrile, Nitromethane) |
| 6 | Proton bound dimers | Moderate MW PIM responders |
| 7 | Monomer Zero $E_C$ crossing point of intermediate and higher MW agents<br>Only stable dimers continue to yield a response but then breakdown<br>Strong Positive $E_C$ shift peak trajectories | Moderate MW PIM responders |
| 8 | Monomers of intermediate MW agents attenuated to below S:N or breakdown | VOCs |
| 9 | Only Monomers of higher MW agents respond<br>Very strong positive Ec shift of monomer trajectories | Nerve agents<br>DNT and other agents with ring structures |

TABLE 2

| Window | Key Information in this window-Peak Behavior (vs $E_D$) | e.g,. Agents responding in this Window |
|---|---|---|
| 1 | Accentuation or attenuation of Zero field Ion Current compared to absence of agent | Accentuation or attenuation of Zero field Ion Current compared to absence of agent |
| 2 | Ion transmission<br>Turn in peak trajectory of low MW agents-resolution from RIP | Electronegative low MW TIC —$Cl_2$, HCl, $F_2$ etc. |
| 3 | Low-mid MW PIM responders ion breakdown | $SO_2$, AcCN, $CH_3NO_2$ |
| 4 | Mid-MW NIM responders-high ion current, breakdown may occur | DMNB, DNT, MS |
| 5 | Mid-Higher NIM responders with ring structures | DNT |

It is also to be appreciated that there may be chemicals which have very similar characteristics, in which case the conditions can be changed (humidity, flow rate, temperature) to provide information to distinguish them.

The above presents a description of a best mode contemplated for carrying out the present invention, and of the manner and process of making and using them, in such full, clear, concise, and exact terms as to enable any person skilled in the art to which it pertains to make and use these devices and methods. The present invention is, however, susceptible to modifications and alternative method steps from those discussed above that are fully equivalent.

Consequently, the present invention is not limited to the particular embodiments disclosed. On the contrary, the present invention encompasses all modifications and alternative constructions and methods coming within the spirit and scope of the present invention. Optional embodiments of the present invention may also be said to broadly consist in the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth.

What is claimed is:

1. An ion filter system, comprising:
   an ion filter;
   a drive signal system for applying drive signals to the ion filter;
   a measurement system for measuring an output of the ion filter; and
   an extraction system coupled to the measurement system adapted to extract numerical parameters from the measured output of the ion filter to facilitate one or more of chemical detection, identification, classification or quantification of gas flow wherein relative peak amplitudes at a plurality of sample flow dilutions are used to infer one or more relative affinities.

2. The ion filter system as recited in claim 1, wherein the one or more inferred relative affinities is used to calculate one or more quantification correction factors.

3. The ion filter system as recited in claim 1, wherein the ion filter is micro-fabricated.

4. The ion filter system as recited in claim 1, wherein a rate of the gas flow through the ion filter is adjustable.

5. The ion filter system as recited in claim 4, wherein the rate of the gas flow is selected to achieve one or more of a desired sensitivity or selectivity.

6. The ion filter system as recited in claim 1, wherein the one or more inferred relative affinities is used in combination with one or more identified or partially identified chemical responses to calculate an affinity of unknown analytes to facilitate the one or more of chemical detection, identification, classification or quantification.

7. An ion filter system, comprising:
   a micro-fabricated ion filter;
   a drive signal system adapted to apply drive signals to the micro-fabricated ion filter;
   a measurement system adapted to measure an output of the micro-fabricated ion filter; and
   an extraction system adapted to extract numerical parameters from the measured output of the micro-fabricated ion filter to facilitate one or more of chemical detection, identification, classification or quantification of gas flow and further adapted to use measurements of ion current as a function of one or more of a compensation field and a dispersion field to facilitate the one or more of chemical detection, identification, classification or quantification.

8. The ion filter system as recited in claim 7, wherein a peak property of an analyte is used in combination with a peak property of a reactant ion to ascertain one or more of identity, class or concentration of the analyte.

9. The ion filter system as recited in claim 7, wherein the micro-fabricated ion filter is configured to separate ions using Field Asymmetric Waveform Ion Mobility Spectrometry (FAIMS) for one or more of detecting, identifying, classifying or quantifying chemical species in the gas flow.

10. The ion filter system as recited in claim 7, wherein a frequency of a waveform of the dispersion field is selected or adjusted to modify effects of humidity on a resulting spectrum.

11. The ion filter system as recited in claim 10, wherein a region of the spectrum used is a region at which a rate of peak width change with respect to the dispersion field undergoes a change.

12. The ion filter system as recited in claim 7, wherein the extraction system adapted to extract the numerical parameters is further adapted to use changes in peak properties as the function of the one or more of the compensation field and the dispersion field to infer a value for mobility of an ion species to facilitate the one or more of chemical detection, identification, classification or quantification.

13. The ion filter system as recited in claim 12, wherein the extraction system adapted to extract the numerical parameters is further adapted to use the inferred mobility value associated with an ion trajectory to create a temperature dependent correction factor that can be applied to the ion trajectory to facilitate the one or more of chemical detection, identification, classification or quantification.

14. The ion filter system as recited in claim 12, wherein the peak properties include one or more of peak height, peak width and peak area.

15. The ion filter system as recited in claim 14, wherein the peak properties are adjusted for changes in ion flux entering the micro-fabricated ion filter.

16. An ion filter system, comprising:
a micro-fabricated ion filter;
a drive signal system adapted to apply drive signals to the micro-fabricated ion filter;
a measurement system adapted to measure an output of the micro-fabricated ion filter; and
an extraction system adapted to extract numerical parameters from the measured output of the micro-fabricated ion filter to facilitate one or more of chemical detection, identification, classification or quantification of gas flow and further adapted to use measurements of ion current as a function of one or more of a compensation field and a dispersion field to facilitate the one or more of chemical detection, identification, classification or quantification wherein a relationship between at least two peak intensities is used to facilitate the one or more of chemical detection, identification, classification or quantification, and further adapted to use a value of the dispersion field at which a dimer peak falls below a threshold value to identify a point of dimer breakdown to facilitate the one or more of chemical detection, identification, classification or quantification.

17. The ion filter system as recited in claim 16, wherein the micro-fabricated ion filter is configured to separate ions using Field Asymmetric Waveform Ion Mobility Spectrometry (FAIMS) for one or more of detecting, identifying, classifying or quantifying chemical species in the gas flow.

18. The ion filter system as recited in claim 16, wherein the extraction system adapted to extract the numerical parameters is further adapted to use an increase in a monomer peak intensity above a certain threshold dispersion field to confirm the dimer breakdown to facilitate the one or more of chemical detection, identification, classification or quantification.

* * * * *